United States Patent
Puckette et al.

(10) Patent No.: US 6,693,219 B2
(45) Date of Patent: Feb. 17, 2004

(54) EPOXIDE STABILIZATION OF FLUOROPHOSPHITE-METAL CATALYST SYSTEM IN A HYDROFORMYLATION PROCESS

(75) Inventors: Thomas Allen Puckette, Longview, TX (US); Ginette Struck Tolleson, Longview, TX (US); Thomas James Devon, Longview, TX (US); Jerome L. Stavinoha, Jr., Longview, TX (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/145,922

(22) Filed: May 15, 2002

(65) Prior Publication Data

US 2003/0018220 A1 Jan. 23, 2003

Related U.S. Application Data

(60) Provisional application No. 60/295,415, filed on Jun. 2, 2001.

(51) Int. Cl.[7] .................. C07C 45/49; C07F 9/02; C07F 7/24; B01J 31/00
(52) U.S. Cl. .................. 568/454; 558/71; 556/2; 556/13; 502/161
(58) Field of Search .................. 568/454; 558/71; 556/2, 13; 502/161

(56) References Cited

U.S. PATENT DOCUMENTS

| | | |
|---|---|---|
| 3,239,566 A | 3/1966 | Slaugh et al. |
| 3,527,809 A | 9/1970 | Pruett et al. |
| 4,482,749 A | 11/1984 | Dennis et al. |
| 4,496,768 A | 1/1985 | Dennis et al. |
| 4,912,155 A | 3/1990 | Burton |
| 5,288,918 A | 2/1994 | Maher et al. |
| 5,364,950 A | 11/1994 | Babin et al. |
| 5,756,855 A | 5/1998 | Abatjoglou et al. |
| 5,840,647 A | 11/1998 | Puckette et al. |
| 5,929,289 A | 7/1999 | Abatjoglou et al. |

OTHER PUBLICATIONS

C. W. Tullock and D. D. Coffman, "Synthesis of Fluorides by Metathesis with Sodium Fluoride", J. Org. Chem, 25, (1960), pp 2016–2019.

D. W. White, R. D. Bertrand, G. K. McEwen, and J. G. Verkade, "Structural Implications of Nuclear Magnetic Resonance Studies on 1–R–1–Phospha–2,6–dioxacyclohexanes" J. Am. Chem. Soc., 92, (1970) pp 7125–7135.

L. Riesel and J. Haenel, "A Simple Synthesis of Fluoro(organyl)phosphanes", J. Z. Anorg. Allg. Chem. 603, pp 145–150, (1991), Berlin, Germany.

T. G. Meyer, A. Fischer, P. G. Jones, and, R. Schmutzler, "Preparation And Single Crystal X–Ray Diffraction Study Of Some Fluorophosphites And Phosphite Esters", Z. Naturforsch, 48b, (1993) pp 659–671.

*Primary Examiner*—James O. Wilson
*Assistant Examiner*—Sikarl A. Witherspoon
(74) *Attorney, Agent, or Firm*—Jonathan D. Wood; Bernard J. Graves, Jr.

(57) ABSTRACT

A process for stabilizing a fluorophosphite ligand in a hydroformylation reaction mixture having an α-olefin, hydrogen, carbon monoxide and a catalyst composition having a combination of a rhodium containing compound and one or more fluorophosphite compounds having the general formula:

(I)

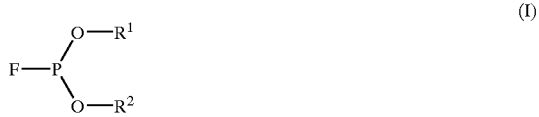

wherein $R^1$ and $R^2$ are hydrocarbyl radicals which contain a total of up to about 40 carbon atoms, the process includes the step of adding to the reaction mixture an epoxide in a sufficient amount to reduce the degradation of the fluorophosphite ligand.

26 Claims, No Drawings

EPOXIDE STABILIZATION OF FLUOROPHOSPHITE-METAL CATALYST SYSTEM IN A HYDROFORMYLATION PROCESS

CROSS REFERENCE TO RELATED APPLICATIONS

Benefit is claimed to the earlier filed application having U.S. Ser. No. 60/295,415 filed Jun. 2, 2001 the entire disclosure of which is incorporated herein by reference.

BACKGROUND OF THE INVENTION

1. Field of the Invention

The present invention relates to a process for stabilizing certain fluorophosphite ligands against degradation. More particularly, the present invention relates to the addition of an epoxide to a homogeneous reaction mixture containing certain fluorophosphite ligands and a Group VIII transition metal catalyst to enhance the stabilization of the fluorophosphite ligands and prevent their degradation. More particularly, the fluorophosphite ligands and rhodium catalyst are used in hydroformylation of various -olefins for producing aldehydes.

2. Background of the Invention

The hydroformylation reaction, also known as the oxo reaction, is used extensively in commercial processes for the preparation of aldehydes by the reaction of one mole of an olefin with one mole each of hydrogen and carbon monoxide. In many of the hydroformylation processes, a catalyst is used that includes a phosphorous containing compound in combination with a Group VIII metal, such as cobalt and rhodium being particularly preferred.

The most extensive use of the hydroformylation reaction is in the preparation of normal- and iso-butyraldehyde from propylene. The ratio of the amount of the normal aldehyde product to the amount of the iso aldehyde product typically is referred to as the normal to iso (N:I) or the normal to branched (N:B) ratio. In the case of propylene, the normal- and iso-butyraldehydes obtained from propylene are in turn converted into many commercially-valuable chemical products, such as, for example, n-butanol, 2-ethyl-hexanol, n-butyric acid, iso-butanol, neo-pentyl glycol, 2,2,4-trimethyl-1,3-pentanediol, and the mono-isobutyrate and di-isobutyrate esters of 2,2,4-trimethyl-1,3-pentanediol. The hydroformylation of higher α-olefins such as 1-octene, 1-hexene and 1-decene yields aldehyde products which are useful feedstocks for the preparation of detergent alcohols and plasticizer alcohols. The hydroformylation of substituted olefins such as allyl alcohol is useful for the production of other commercially valuable products such as 1,4-butanediol.

U.S. Pat. No. 3,239,566, issued Mar. 8, 1966, to Slaugh and Mullineaux, discloses a low pressure hydroformylation process using trialkylphosphines in combination with rhodium catalysts for the preparation of aldehydes. Trialkylphosphines have seen much use in industrial hydroformylation processes but they typically produce a limited range of products and, furthermore, frequently are very oxygen sensitive.

U.S. Pat. No. 3,527,809, issued Sep. 8, 1970 to Pruett and Smith, discloses a low pressure hydroformylation process which utilizes triarylphosphine or triarylphosphite ligands in combination with rhodium catalysts. The ligands disclosed by Pruett and Smith, although used in many commercial applications, have limitations due to oxidative and hydrolytic stability problems. Since these early disclosures, numerous improvements have been made to increase the catalyst stability, catalyst activity and the product ratio with a heavy emphasis on yielding linear aldehyde product. A wide variety of monodentate phosphite and phosphine ligands, bidentate ligands such as bisphosphites and bisphosphines as well as tridentate and polydentate ligands have been prepared and disclosed in the literature.

U.S. Pat. No. 5,840,647 issued Nov. 24, 1998 to Puckette et al. discloses a fluorophosphite-containing catalyst system having a catalyst combination of one or more transition metals selected from the Group VIII metals and/or rhenium and one or more fluorophosphite compounds having the general formula:

(I)

wherein $R^1$ and $R^2$ are hydrocarbyl radicals which contain a total of up to about 40 carbon atoms and wherein the ratio of gram moles fluorophosphite ligand to gram atoms transition metal is at least 1:1. As will be understood by those skilled in the art, such fluorophosphite compounds of structure (I) are also known in the chemical literature as fluorophosphite esters and such terms are used interchangeably herein.

A problem recently recognized in hydroformylation of α-olefins is that phosphite ligands can be depleted through reaction with components in the hydroformylation reaction mixture. For example, U.S. Pat. No. 4,496,768 postulates the formation of adducts of certain phosphites with aldehydes. U.S. Pat. Nos. 4,496,768 and 4,482,749 disclose certain cyclic phosphite ligands are capable of operating for extended periods of time in hydroformylation reaction mixtures with little or no degradation of the ligand.

It has been observed that the ligand undergoes slow hydrolysis in the presence of water in the reaction mixture. The decomposition products then react with the aldehyde product and additional water in the reaction mixture in a series of steps to form hydroxyalkylphosphonic acids. The acids so formed catalyze further hydrolysis of the ligand. The cascading effect causes very rapid hydrolysis of the phosphite ligand remaining in the reaction solution and leads to a significant loss of the phosphite ligand.

U.S. Pat. No. 5,288,918, issued to Maher et al. on Feb. 22, 1994, discloses that catalytic deactivation is believed primarily or at least partly due to the formation of a class of diorganophosphite by-products which can best be described as decomposition by-products of alkyl (1,1'-biaryl-2,2'-diyl) phosphites, the alkyl radical corresponding to the particular n-aldehyde produced by the hydroformylation process and the (1,1'-biaryl-2,2'-diyl) portion of the phosphite being derived from the organobisphosphite ligand employed. Maher teaches that the adverse effects of such compounds can be reversed or minimized by carrying out the hydroformylation process in the presence of weakly acidic compounds, added water or mixtures of both. The weakly acidic compounds have a pKa of from about 1.0 to about 12.

U.S. Pat. No. 5,756,855, issued on May 26, 1998 to Abatjoglou et al., discloses stabilizing phosphite degradation by the addition of certain metals. Abatjoglou discloses adding a Group VIII metal (other than rhodium) in an amount sufficient to reduce the rhodium-catalyzed decomposition of the phosphite during the hydroformylation process.

U.S. Pat. No. 5,364,950, issued on Nov. 15, 1994 to Babin et al., discloses stabilizing a triorganophosphites, diorganophosphites and bis-phosphites phosphite ligand wherein the phosphorous moiety is bound to three oxygen moieties. However, the '950 patent is silent as to what effect, if any, an epoxide may have to stabilize a fluorophosphite ligand in which a secondary acid, i.e., hydrofluoric acid, may be present in the reaction mixture.

Accordingly, there is a need for a process for stabilizing certain fluorophosphite ligands against degradation when used in a hydroformylation reaction.

SUMMARY OF THE INVENTION

Briefly, the process of the present invention is for stabilizing a fluorophosphite ligand in a hydroformylation reaction mixture containing an olefinic compound, carbon monoxide, hydrogen, a catalyst composition comprising a combination of a transition metal selected from the Group VIII metals and one or more fluorophosphite compounds having the general formula:

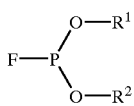
(I)

wherein $R^1$ and $R^2$ are hydrocarbyl radicals which contain a total of up to about 40 carbon atoms by adding to the reaction mixture an epoxide.

Surprisingly, it was found that the addition of an epoxide to the hydroformylation reaction mixture was effective in markedly lowering the production of phosphorous acids and hydrofluoric acid without detrimental reaction with the aldehyde product.

It is an object of the present invention to provide a process for stabilizing a fluorophosphite ligand in a hydroformylation reaction mixture. This and other objects and advantages of the present invention will become more apparent to those skilled in the art in view of the following description. It is to be understood that the inventive concept is not to be considered limited to the constructions disclosed herein but instead by the scope of the appended claims.

DETAILED DESCRIPTION OF THE INVENTION

The fluorophosphite ligand-containing transition metal catalysts to which the process of the present invention is applicable are used to promote and catalyze a number of reactions. For convenience, details of the process of the present invention are, to some extent, described herein in particular as they relate to catalysts used in the hydroformylation of olefins to form aldehydes. However, the invention is not limited to the stabilization of fluorophosphite-containing catalysts utilized in olefin hydroformylation. Rather, the invention is also related to various other reaction mixtures for homogeneous catalysis where there exists a need to reduce the degradation of fluorophosphite ligand-containing catalysts.

The catalyst system includes a combination of a transition metal selected from the Group VIII transition metals and one or more fluorophosphite compounds briefly described above. The transition metal may be provided in the form of various metal compounds such as carboxylate salts of the transition metal. Rhodium is the preferred Group VIII metal. The source of rhodium for the active catalyst include rhodium II or rhodium III salts of carboxylic acids, examples of which include di-rhodium tetraacetate dihydrate, rhodium (II) acetate, rhodium(II) isobutyrate, rhodium(II) 2-ethylhexanoate, rhodium(II) benzoate and rhodium(II) octanoate. Also, rhodium carbonyl species such as $Rh_4(CO)_{12}$, $Rh_6(CO)_{16}$ and rhodium(I) acetylacetonate dicarbonyl may be suitable sources of rhodium. Additionally, rhodium organophosphine complexes such as tris (triphenylphosphine) rhodium carbonyl hydride may be used when the phosphine moieties of the complex feed are easily displaced by the fluorophosphite ligands of the present invention. Other rhodium sources include rhodium salts of strong mineral acids such as chlorides, bromides, nitrates, sulfates, phosphates and the like. Rhodium 2-ethylhexanoate is a particularly preferred source of rhodium from which to prepare the complex catalyst of the invention because it is a convenient source of soluble rhodium, as it can be efficiently prepared from inorganic rhodium salts such as rhodium halides.

The fluorophosphite ligands useful in the process of the present invention having the general formula:

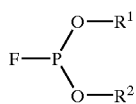
(I)

wherein $R^1$ and $R^2$ are hydrocarbyl radicals which contain a total of up to about 40 carbon atoms and wherein the ratio of gram moles fluorophosphite ligand to gram atoms transition metal is at least 1:1.

Fluorophosphite compounds function as effective ligands when used in combination with transition metals to form catalyst systems for the processes described hereinabove. The hydrocarbyl groups represented by $R^1$ and $R^2$ may be the same or different, separate or combined, and are selected from unsubstituted and substituted alkyl, cycloalkyl and aryl groups containing a total of up to about 40 carbon atoms. The total carbon content of substituents $R^1$ and $R^2$ preferably is in the range of about 2 to 35 carbon atoms. Non-limiting examples of alkyl groups which $R^1$ and/or $R^2$ independently can be selected from include ethyl, butyl, pentyl, hexyl, 2-ethylhexyl, octyl, decyl, dodecyl, octadecyl and various isomers thereof. The alkyl groups may be substituted, for example, with up to two substituents such as alkoxy, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts and the like. Cyclopentyl, cyclohexyl and cycloheptyl are examples of the cycloalkyl groups $R^1$ and/or $R^2$ individually can represent. The cycloalkyl groups may be substituted with alkyl or any of the substituents described with respect to the possible substituted alkyl groups. The alkyl and cycloalkyl groups which $R^1$ and/or $R^2$ individually can represent preferably are alkyl of up to about 8 carbon atoms, benzyl, cyclopentyl, cyclohexyl or cycloheptyl.

Examples of the aryl groups which $R^1$ and/or $R^2$ individually can represent include carbocyclic aryl such as phenyl, naphthyl, anthracenyl and substituted derivatives thereof. Examples of the carbocyclic aryl groups which $R^1$ and/or $R^2$ individually can represent the radicals having the formulas:

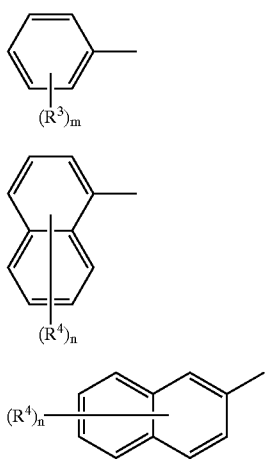

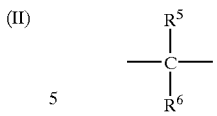

wherein $R^3$ and $R^4$ may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts and the like. The alkyl moiety of the aforesaid alkyl, alkoxy, alkanoyl, alkoxycarbonyl and alkanoyloxy groups typically contains up to about 8 carbon atoms. Although it is possible for m to represent 0 to 5 and for n to represent 0 to 7, the value of each of m and n usually will not exceed 2. $R^3$ and $R^4$ preferably represent lower alkyl groups, i.e., straight-chain and branched-chain alkyl of up to about 4 carbon atoms, and m and n each represent 0, 1 or 2.

Alternatively, $R^1$ and $R^2$ in combination or collectively may represent a divalent hydrocarbylene group containing up to about 40 carbon atoms, preferably from about 12 to 36 carbon atoms. Examples of such divalent groups include alkylene of about 2 to 12 carbon atoms, cyclohexylene and arylene. Specific examples of the alkylene and cycloalkylene groups include ethylene, trimethylene, 1,3-butanediyl, 2,2-dimethyl-1,3-propanediyl, 1,1,2-triphenylethanediyl, 2,2,4-trimethyl-1,3-pentanediyl, 1,2-cyclohexylene, and the like. Examples of the arylene groups which $R^1$ and $R^2$ collectively may represent are given herein below as formulas (V), (VI) and (VII).

The divalent groups that $R^1$ and $R^2$ collectively may represent include radicals having the formula:

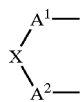

wherein $A^1$ and $A^2$ independently can be an arylene radical, e.g., a divalent, carbocyclic aromatic group containing 6 to 10 ring carbon atoms, wherein each ester oxygen atom of fluorophosphite (I) is bonded to a ring carbon atom of $A^1$ and $A^2$.

X is (i) a chemical bond directly between ring carbon atoms of $A^1$ and $A^2$; or (ii) an oxygen atom, a group having the formula —$(CH_2)_y$— wherein y is 2 to 4 or a group having the formula:

wherein $R^5$ is hydrogen, alkyl or aryl, e.g., the aryl groups illustrated by formulas (II), (III) and (IV), and $R^6$ is hydrogen or alkyl. The total carbon content of the group —$C(R^5)(R^6)$— normally will not exceed 20 and, preferably, is in the range of 1 to 8 carbon atoms. Normally, when $R^1$ and $R^2$ collectively represent a divalent hydrocarbylene group, the phosphite ester oxygen atoms, i.e. the oxygen atoms depicted in formula (I), are separated by a chain of atoms containing at least 3 carbon atoms.

Examples of the arylene groups represented by each of $A^1$ and $A^2$ include the divalent radicals having the formulas:

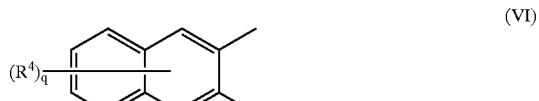

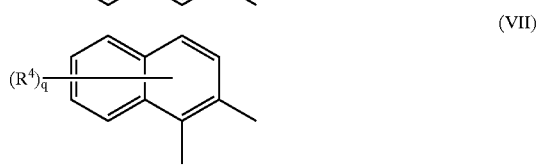

wherein $R^3$ and $R^4$ may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts and the like. The alkyl moiety of such alkyl, alkoxy, alkanoyl, alkoxycarbonyl and alkanoyloxy groups typically contains up to about 8 carbon atoms. Although it is possible for p to represent 0 to 4 and for q to represent 0 to 6, the value of each of p and q usually will not exceed 2. $R^3$ and $R^4$ preferably represent lower alkyl groups, i.e., straight-chain and branched-chain alkyl of up to about 4 carbon atoms, and p and q each represent 0, 1 or 2.

The fluorophosphite compounds that are most preferred, e.g., those which exhibit the best stability, are those wherein the fluorophosphite ester oxygen atoms are bonded directly to a ring carbon atom of a carbocyclic, aromatic group, e.g., an aryl or arylene group represented by any of formulas (II) through (VII). When $R^1$ and $R^2$ individually each represents an aryl radical, e.g., a phenyl group, it is further preferred that 1 or both of the ring carbon atoms that are in a position ortho to the ring carbon atoms bonded to the fluorophosphite ester oxygen atom are substituted with an alkyl group, especially a branched chain alkyl group such as isopropyl, tert-butyl, tert-octyl and the like. Similarly, when $R^1$ and $R^2$ collectively represent a radical having the formula:

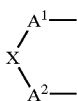

the ring carbon atoms of arylene radicals $A^1$ and $A^2$ that are in a position ortho to the ring carbon atoms bonded to the fluorophosphite ester oxygen atom are substituted with an alkyl group, preferably a branched chain alkyl group such as isopropyl, tert-butyl, tert-octyl and the like.

The most preferred fluorophosphites have the general formula:

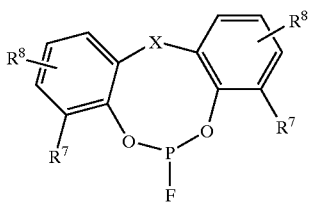

wherein $R^7$ is independently selected from an alkyl of 3 to 8 carbon atoms; $R^8$ is independently selected from hydrogen, an alkyl having from 1 to 8 carbon atoms or an alkoxy having 1 to 8 carbon atoms; and X is (i) a chemical bond directly between ring carbon atoms of each phenylene group to which X is bonded; or (ii) a group having the formula:

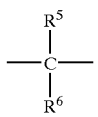

wherein $R^5$ and $R^6$ independently are selected from hydrogen or alkyl having from 1 to 8 carbon atoms.

The fluorophosphites of formula (I) may be prepared by published procedures or by techniques analogous thereto. See, for example, the procedures described by Riesel et al., J. Z. Anorg. Allg. Chem., 603, 145 (1991), Tullock et al., J. Org. Chem., 25, 2016 (1960), White et al., J. Am. Chem. Soc., 92, 7125 (1970) and Meyer et al., Z. Naturforsch, Bi. Chem. Sci., 48, 659 (1993) and in U.S. Pat. No. 4,912,155. The organic moiety of the fluorophosphite compounds, i.e., the residue(s) represented by $R^1$ and $R^2$ can be derived from chiral or optically active compounds. Fluorophosphite ligands derived from chiral glycols or phenols will also be chiral and will generate chiral catalyst complexes.

No special provisions are required for the preparation of the catalyst employed in the practice of the present invention, although it is preferred, for high catalyst activity, that all manipulations of the rhodium and fluorophosphite components be carried out under an inert atmosphere, e.g., $N_2$, Ar, and the like. The desired quantities of a suitable rhodium compound and ligand are charged to the reactor in a suitable solvent. The sequence in which the various catalyst components or reactants are charged to the reactor is not critical.

The process of the present invention can be carried out with widely varied amounts of rhodium and ligand present in the reaction mixture. For example, amounts of catalyst containing as little as about $1\times10^{-6}$ moles of rhodium (calculated based on rhodium metal) per mole of olefin in the reactor zone can be employed. Concentrations in the range of about $1\times10^{-5}$ to about $5\times10^{-2}$ moles of rhodium per mole of olefin are preferred. Rhodium concentrations in the range of about $1\times10^{-4}$ Up to $1\times10^{-3}$ are most preferred because most efficient utilization of rhodium is obtained while the cost of the rhodium component is maintained within a commercially reasonable amount.

The molar ratios of ligand to rhodium will vary within the range of about 1 to about 100. Preferably the molar ratio of ligand to rhodium will vary within the range from about 10 to about 70. In a most preferred embodiment, the molar ratio of ligand to rhodium will be from about 15 to about 50.

Epoxides suitably utilized in the process of the present invention have the general formula:

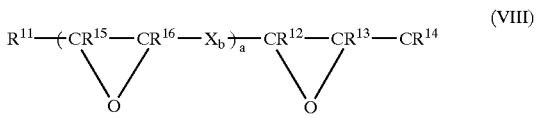

wherein: "a" and "b" are independently 0 or 1; $R^{11}$–$R^{16}$ are independently selected from the group consisting of hydrogen; monovalent hydrocarbon radicals, such as, alkyl, aryl, aralkyl, and alkaryl groups having from 1 to about 30 carbon atoms; substituted alkyl, aryl, aralkyl and alkaryl groups having from 1 to about 30 carbon atoms; and groups wherein two or more of $R^{11-R16}$ are linked together to form a cyclic structure which has up to about 30 carbon atoms and which may comprise a plurality of ring structures such as bicyclo-, tricyclo-, tetracyclo- and n-cyclo- groups; and "X" is a divalent bridging group selected from the group consisting of substituted or unsubstituted alkylene, arylene, aralkylene, and alkarylene groups having up to about 30 carbon atoms, —O—, —S—, —$NR^{19}$—, —$SiR^{20}$ $R^{21}$, and —CO— and wherein each radical $R^{19}$, $R^{20}$, and $R^{21}$ individually represents H or alkyl groups.

In this definition, the word "substituted" denotes presence of groups which do not react with epoxides, such as alkoxy and aryloxy groups. Excluded from the definition of "substituted" are halogens, carboxyl moieties, nitrile groups, and any other moieties which react with epoxides. Hydrocarbon epoxides are preferred.

When "a" and "b" equal 0 in formula (VIII) above, epoxides suitable used in the process of this invention have the formula:

wherein $R^{11}$–$R^{14}$ are as described above with regard to formula (VIII). Examples of suitable epoxides of formula (IX) include, but are not limited to, 1,2-cyclohexene oxide; styrene oxide; propylene oxide; 1,2-epoxyoctane; 1,2-epoxydecane; 1,2-epoxydodecane; 1,2-epoxyhexadecane; 1,2-epoxyoctadecane; ethylene oxide; 1,2-cyclododecene oxide; stilbene oxide; isobutylene oxide; 2,3-epoxybutane; 1,2-epoxybutane; 1,2-epoxyhexane; 1,2-epoxydodecane; cyclopentene oxide; cyclooctene oxide; cyclodecene oxide; and 1,2-epoxy-3-phenoxy-propane.

Epoxy compositions of formula (IX) above having at least one ring in a cyclic structure formed by the combination of one of $R^{11}$ and $R^{12}$ groups with one of $R^{13}$ and $R^{14}$ groups include cyclic structures which have a plurality of rings associated therewith, including bicyclo- and other n-cyclo-groups. Bicyclo-groups are cyclic hydrocarbon groups consisting of two rings only having two or more atoms in common. Tricyclo-, tetracyclo-, and other n-cyclo- compounds also are included within the definition of cyclic structures having a plurality of rings. Examples of such plural ring structures within the scope of a cyclic structure formed by the combination of one of $R^{11}$ and $R^{12}$ groups with one of $R^{13}$ and $R^{14}$ groups include the bicyclo- compounds norbornane and α-pinene. Epoxy compounds suitable for use in the subject invention which are formed from norbornane and α-pinene are 2,3-epoxynorbornane and α-pinene oxide.

Epoxy compounds useful in the process of this invention include those having a composition of formula (IX) above, wherein the $R^{11}$ and $R^{12}$ groups together or the $R^{13}$ and $R^{14}$ groups together, or both, may form cyclic structure(s) which may include a plurality of rings. The cyclic structure of such compounds can include bicyclo-, tricyclo-, and other n-cyclo compounds. Pinene is a composition having a ring structure which yields an epoxy compound useful in the present invention. The epoxy compound derived from pinene, β-pinene oxide, is a compound of formula (IX) above wherein $R^{11}$ and $R^{12}$ form a cyclic structure having a plurality of ring structures, $R^{13}$ is a methyl group, and $R^{14}$ is hydrogen.

Diepoxides also are useful in the method of the invention. Suitable diepoxy compounds of formula (VIII) include 1,3-butadiene diepoxide, 1,2,7,8-diepoxyoctane, diepoxycyclooctane, dicyclopentadiene dioxide, and 3,4-epoxy cyclohexyl methyl-3,4-epoxy cyclohexyl carboxylate, vinylcyclohexene diepoxide, and hydroquinone bisglycidyl ether.

The amount of epoxide utilized in accordance with the process should be sufficient to interact with the strong acids which cause degradation of phosphite ligand-containing catalysts. Preferably, the quantity of epoxide is sufficient to maintain the concentration of strong acidic by-products below the threshold level which causes rapid degradation of the ligand, and preferably below 0.2 milliequivalents per liter. Desirably, the quantity of epoxide added is sufficient to maintain the concentration of strong acidic by-products below 0.15 milliequivalents per liter.

A suitable concentration of epoxide in a hydroformylation reaction mixture used in the present invention typically is from about 0.001 to about 1.0 weight percent of the total weight of reaction mixture, and preferably from about 0.01 to about 0.8 weight percent of the total weight of reaction mixture. Desirably, the maximum epoxide concentration is limited by practical considerations, such as the cost of epoxide and avoidance of undesirable side effects from too much epoxide (e.g., the formation of acetal and polyether byproducts and the possible contamination of the desired product with excess epoxide). The concentration of epoxide preferably equals, and more preferably somewhat exceeds, a stoichiometric concentration required for the epoxide to interact with each strong acid molecule produced during phosphite degradation. Typically, one epoxide group is required to interact with each phosphorous acid and hydrofluoric acid molecule. An excess of epoxide typically is not harmful and a stoichiometric deficiency of epoxide merely limits the effectiveness of the invention.

As used herein, a "strong acid" is any acid having an aqueous dissociation constant, pKa, that is less than 4.5. A suitable method for measuring the concentration of the strongly acidic materials in the oxo reaction mixture is as follows:

The analysis uses a potentiometric, pH-based, titration in combination with controlled extraction using aqueous sodium 2-ethylhexanoate solution to selectively react with the strongly acidic material present in an organic solution. The basic calculation method determines the amount of sodium 2-ethylhexanoate that is neutralized by the amount of strong acid present in a given sample and uses that value to determine the concentration of acid present in the sample.

For example, a stock solution of aqueous sodium 2-ethylhexanoate was prepared by the addition of 0.837 grams of solid sodium 2-ethylhexanoate to 0.500 liter of deionized water. This material was standardized by normal potentiometric titration methods by dissolving a 2.0 ml sample of the stock solution in 50 ml of reagent grade methanol and titrating with standardized 0.005 N aqueous hydrochloric acid. The concentration of sodium 2-ethylhexanoate was 0.0082 milliequivalents/milliliter. This normality is $N_{init}$.

Extraction and analysis was carried out by the following method. Catalyst handling and extraction is carried out in an inert atmosphere, such as a nitrogen box. A clean 250 ml glass separator funnel was charged with 50.0 ml sample of the catalyst solution. To this was added 25 ml of reagent grade n-heptane and 10.0 ml of the standardized sodium 2-ethylexanoate solution described above. This mixture was shaken vigorously for two minutes and the two clear phases were allowed to separate. The lower, aqueous phase was drained and collected in a clean glass bottle. Two milliliters of this aqueous extract were added to 50 ml of reagent grade methanol. This was potentiometrically titrated with standardized aqueous 0.005 N hydrochloric acid to determine the final concentration of sodium 2-ethylhexanoate in the water phase. The final concentration of 0.0067 meg/liter is $N_{final}$. The calculation below was used to calculate the concentration of strong acid in milliequivalents/liter in this particular reactor sample.

$$((N_{init}-N_{final}) \times 10 \text{ ml extract} \times 1000 \text{ ml/liter})/50 \text{ ml sample} = 0.30 \text{ meq H}^+/L$$

In the process of the present invention, the epoxide is added to the reactor and thoroughly mixed into the reaction mixture using any convenient procedure. The epoxide can be mixed with or dissolved in any of the reactant streams or solvent make-up streams or the epoxide periodically can be separately added to the reactant mixture. The epoxide can be added to the reaction mixture in small quantities over an extended period of operation. In this way, a concentration of epoxide effective to stabilize ligand during steady-state operation is obtained, with epoxide consumed by reaction with phosphorous acid as it is formed. The epoxide also can be added intermittently at a higher concentration, with the intent of achieving a long-term stabilization effect by starting at a higher-than-necessary concentration and allowing the concentration to fall to a more typical concentration during a period without epoxide addition.

A suitable solvent may be used in the process of the invention that does not adversely affect the hydroformylation process and which is inert with respect to the catalyst, olefin, hydrogen, and carbon monoxide feeds as well as the hydroformylation products. Inert solvents of this nature are well known to those of skill in the art and include such solvents as benzene, xylene, toluene, as well as their substituted derivatives; pentanes, naphtha, kerosene, mineral oils, cyclohexane, cyclopentane, ethers, esters, etheresters, alcohols, acetals, ketones, water, as well as various mixtures thereof. Preferred solvents for the hydroformylation reaction to form volatile aldehydes include such compounds as dioctylphthalate, 2,2,4-trimethyl-1,3-pentanediol monoisobutyrate and its isomers, as well as the by-products of the hydroformylation reaction, such as alcohols, esters, acetals and hydroxyaldehydes which are retained as high boiling liquids at the bottom of subsequent distillation columns. Preferred solvents and solvent combinations for less volatile and non-volatile aldehyde products include 1-methyl-2-pyrrolidinone, dimethylformamide, perfluorinated solvents such as perfluorokerosene, sulfolane, water, and high boiling hydrocarbon liquids as well as combinations of these solvents.

The reaction conditions used are not critical for the operation of the process and conventional hydroformylation conditions normally are used. The process requires that an olefin is contacted with hydrogen and carbon monoxide in the presence of the catalyst system described above and an epoxide.

The olefins that may be hydroformylated include aliphatic, including ethylenically-unsaturated, low molecular weight polymers, alicyclic, aromatic and heterocyclic mono-, di- and tri-olefins containing up to about 40 carbon atoms. Examples of the aliphatic olefins that may be utilized in the process include straight- and branched-chain, unsubstituted and substituted, aliphatic mono-α-olefins containing up to about 20 carbon atoms and non-conjugated polyolefins typically having in the range of 5 up to 5,000 carbon atoms, e.g., polybutadiene, with each of the above optionally containing groups or substituents which do not interfere with the hydroformylation process. Such substituents include: ethers, esters, amides, acetals, ketals, tertiary amines, ketones, aldehydes, nitriles alcohols and carboxylic acids.

Substituted olefins such allyl alcohol, methyl methacrylate, methyl acrylate, allyl acetate, 4-hydroxybutene-1, may be used in this invention. Other feedstocks include branched olefins such as isobutene, cis-2-butene. Diolefins such as 1,7-octadiene and the like may also be used to prepare dialdehyde products provided that the two carbon-carbon double bonds are not in conjugation. Normal or linear aldehyde products may be formed by the hydroformylation of the mixtures of internal olefins. For example, the hydroformylation of mixtures of cis and trans 2-octene was found to yield a product mixture containing n-nonyl aldehyde.

Mixtures of olefins can also be used in the practice of this invention. The mixtures may be of the same carbon number such as mixtures of n-octenes or it may represent refinery distillation cuts that will contain a mixture of olefins over a range of several carbon numbers.

The amount of olefin present in the reaction mixture also is not critical. For example, relatively high-boiling olefins such as 1-octene may function both as the olefin reactant and the process solvent. In the hydroformylation of a gaseous olefin feedstock such as propylene, the partial pressures in the vapor space in the reactor typically are in the range of about 0.07 to 35 bars absolute. In practice the rate of reaction is favored by high concentrations of olefin in the reactor. In the hydroformylation of propylene, the partial pressure of propylene preferably is greater than 1.4 bars, e.g., from about 1.4 to 10 bars absolute. In the case of ethylene hydroformylation, the preferred partial pressure of ethylene in the reactor is greater than 0.14 bars absolute.

While the process may be carried out at temperatures in the range of about 20° to 200° C., the preferred hydroformylation reaction temperatures are from 50° to 135° C. with the most favored reaction temperatures ranging from 75° to 125° C. Higher reactor temperatures are not favored because of increased rates of catalyst decomposition while lower reactor temperatures result in relatively slow reaction rates. The total reaction pressure may range from about ambient or atmospheric up to 70 bars absolute (about 1000 psig). Preferably the total reaction pressure is from about 8 to 28 bars absolute (about 100 to 400 psig).

The hydrogen:carbon monoxide mole ratio in the reactor likewise may vary considerably ranging from 10:1 to 1:10 and the sum of the absolute partial pressures of hydrogen and carbon monoxide may range from 0.3 to 36 bars absolute. The partial pressures of the ratio of the hydrogen to carbon monoxide in the feed is selected according to the linear:branched isomer ratio desired. Generally, the partial pressure of hydrogen and carbon monoxide in the reactor is maintained within the range of about 1.4 to 13.8 bars absolute (about 20 to 200 psia) for each gas. The partial pressure of carbon monoxide in the reactor is maintained within the range of about 1.4 to 13.8 bars absolute (about 20 to 200 psia) and is varied independently of the hydrogen partial pressure. The molar ratio of hydrogen to carbon monoxide can be varied widely within these partial pressure ranges for the hydrogen and carbon monoxide. The ratios of the hydrogen to carbon monoxide and the partial pressure of each in the synthesis gas (syngas—carbon monoxide and hydrogen) can be readily changed by the addition of either hydrogen or carbon monoxide to the syngas stream. We have found that with the fluorophosphite ligands described herein, the ratio of linear to branched products can be varied widely by changing the partial pressures of the carbon monoxide in the reactor.

Any of the known hydroformylation reactor designs or configurations may be used in carrying out the process provided by the present invention. Thus, a gas-sparged, vapor take-off reactor design may be used. In this mode of operation, the catalyst which is dissolved in a high boiling organic solvent under pressure does not leave the reaction zone with the aldehyde product taken overhead by the unreacted gases. The overhead gases then are chilled in a vapor/liquid separator to liquefy the aldehyde product and the gases can be recycled to the reactor. The liquid product is let down to atmospheric pressure for separation and purification by conventional technique. The process also may be practiced in a batch wise manner by contacting the olefin, hydrogen and carbon monoxide with the present catalyst in an autoclave.

A reactor design where catalyst and feedstock are pumped into a reactor and allowed to overflow with product aldehyde, i.e. liquid overflow reactor design, is also suitable. For example, high boiling aldehyde products such a nonyl aldehyde may be prepared in a continuous manner with the aldehyde product being removed from the reactor zone as a liquid in combination with the catalyst. The aldehyde product may be separated from the catalyst by conventional means such as by distillation or extraction and the catalyst then recycled back to the reactor. Water soluble aldehyde products, such as hydroxy butyraldehyde products obtained by the hydroformylation of allyl alcohol, can be separated from the catalyst by extraction techniques. A trickle-bed reactor design also is suitable for this process. It will be apparent to those skilled in the art that other reactor schemes may be used with this invention.

The present invention is illustrated in greater detail by the specific example presented below. It is to be understood that the example is an illustrative embodiment is not intended to be limiting of the invention, but rather are to be construed broadly within the scope and content of the appended claims.

In a continuous process for the hydroformylation of α-olefins to produce aldehydes, a catalyst was prepared having a transition metal selected from a Group VIII metal and one or more fluorophosphite compounds described above. The catalyst and fluorophosphite compounds were prepared in accordance with the teaching of U.S. Pat. No. 5,840,647, the entire disclosure of which is incorporated herein by reference.

The continuous process was started up and allowed to run without any epoxide present until the presence of a strong acid and HF production became detrimental to the production of the aldehyde, approximately 29 days. The amount of HF produced per day had also increased from 0.46 grams per day to 0.57 grams per day over the preceding 10 days.

On day 30 an epoxide, (1,2-epoxydodecane), was added to the reactor to raise the level of epoxide in the reactor to about 0.10 weight %, with a continuous addition of epoxide thereafter to maintain a level of epoxide in the reactor in the range of from about 0.05 to less than about 0.2 weight % of the total reaction mixture. The results of the shown in Table I below.

TABLE I

| Day | Strong Acid, mmole/Liter | Epoxide, % of reactor | Grams HF generated |
|---|---|---|---|
| 1 | | | 0.502 |
| 2 | | | 0.136 |
| 3 | | | 0.157 |
| 4 | 0.01 | 0 | 0.161 |
| 5 | 0.01 | 0 | 0.154 |
| 6 | | 0 | 0.17 |
| 7 | 0.01 | 0 | 0.189 |
| 8 | | 0 | 0.213 |
| 9 | | 0 | 0.239 |
| 10 | | 0 | 0.26 |
| 11 | 0.01 | 0 | 0.29 |
| 12 | 0.02 | 0 | 0.326 |
| 13 | 0.01 | 0 | 0.349 |
| 14 | 0.01 | 0 | 0.344 |
| 15 | 0.01 | 0 | 0.347 |
| 16 | | 0 | 0.325 |
| 17 | | 0 | 0.371 |
| 18 | | 0 | 0.411 |
| 19 | 0.01 | 0 | 0.45 |
| 20 | 0.01 | 0 | 0.485 |
| 21 | 0.01 | 0 | 0.461 |
| 22 | 0.01 | 0 | 0.482 |
| 23 | 0.04 | 0 | 0.505 |
| 24 | | 0 | 0.525 |
| 25 | 0.02 | 0 | 0.505 |
| 26 | 0.01 | 0 | 0.497 |
| 27 | 0.01 | 0 | 0.562 |
| 28 | 0.05 | 0 | 0.554 |
| 29 | 0.08 | 0 | 0.567 |
| 30 | 0.1 | 0.09 | 0.575 |
| 31 | | 0.07 | 0.575 |
| 32 | | 0.07 | 0.605 |
| 33 | 0.03 | 0.07 | 0.545 |
| 34 | 0.01 | 0.065 | 0.521 |
| 35 | 0.01 | 0.065 | 0.515 |
| 36 | 0.01 | 0.058 | 0.491 |
| 37 | 0.14 | 0.054 | 0.472 |
| 38 | | 0.05 | 0.481 |
| 39 | | 0.049 | 0.434 |
| 40 | 0.19 | 0.124 | 0.483 |
| 41 | 0.003 | 0.107 | 0.41 |
| 42 | 0.15 | 0.086 | 0.44 |
| 43 | 0.12 | 0.07 | 0.474 |
| 44 | 0.07 | 0.062 | 0.532 |
| 45 | | 0.059 | 0.504 |
| 46 | | 0.063 | 0.487 |
| 47 | 0.01 | 0.077 | 0.485 |
| 48 | 0.13 | 0.073 | 0.434 |
| 49 | 0.16 | 0.106 | 0.45 |
| 50 | 0.13 | 0.097 | 0.45 |
| 51 | 0.11 | 0.1 | 0.434 |
| 52 | | 0.089 | 0.433 |
| 53 | | 0.082 | 0.463 |
| 54 | 0.11 | 0.104 | 0.463 |

TABLE I-continued

| Day | Strong Acid, mmole/Liter | Epoxide, % of reactor | Grams HF generated |
|---|---|---|---|
| 55 | 0.11 | 0.099 | 0.493 |
| 56 | 0.12 | | 0.489 |
| 57 | | | 0.447 |
| 58 | | 0.103 | 0.46 |
| 59 | | 0.106 | 0.463 |
| 60 | | 0.1 | 0.457 |
| 61 | 0.11 | 0.118 | 0.477 |
| 62 | 0.14 | 0.103 | 0.434 |
| 63 | 0.11 | 0.098 | 0.441 |
| 64 | 0.12 | 0.093 | 0.45 |
| 65 | 0.16 | 0.115 | 0.45 |
| 66 | | 0.108 | 0.389 |
| 67 | | 0.1 | 0.396 |
| 68 | | 0.096 | 0.419 |
| 69 | 0.14 | 0.093 | 0.415 |

As the data above shows, the amount of HF produced declined appreciably over the subsequent 40 days, having approximately a 33% decrease in HF daily production. More importantly, the reactor continued to operate in a steady lined out manner with as little as 0.10 weight % epoxide in the reactor.

The above data further illustrates that the: 1) addition of an epoxide reduces the production of both HF and the strong acid; 2) continuous addition of epoxide to maintain a low level of epoxide in the reactor will hold the strong acid and the HF production at manageable, steady levels without autocatalytic degradation of the fluorophosphite ligand; and 3) total removal of all strong acid is not necessary for steady operations.

Having described the invention in detail, those skilled in the art will appreciate that modifications may be made to the various aspects of the invention without departing from the scope and spirit of the invention disclosed and described herein. It is, therefore, not intended that the scope of the invention be limited to the specific embodiments illustrated and described but rather it is intended that the scope of the present invention be determined by the appended claims and their equivalents. Moreover, all patents, patent applications, publications, and literature references presented herein are incorporated by reference in their entirety for any disclosure pertinent to the practice of this invention.

We claim:

1. In a hydroformylation process having a reaction mixture which includes a catalyst composition comprising a combination of a transition metal compound selected from the Group VIII metals and one or more fluorophosphite compounds having the general formula:

(I)

wherein $R^1$ and $R^2$ are hydrocarbyl radicals which contain a total of up to about 40 carbon atoms wherein the improvement comprises stabilizing said fluorophosphite compounds by adding to the reaction mixture an epoxide.

2. The process of claim 1 wherein said Group VIII metal compound is selected from the group consisting of di-rhodium tetraacetate dihydrate, rhodium(II) acetate, rhodium(II) isobutyrate, rhodium(II) 2-ethylhexanoate, rhodium(II) benzoate, rhodium(II) octanoate, $Rh_4(CO)_{12}$, $Rh_6(CO)_{16}$ and rhodium(I) acetylacetonate dicarbonyl.

3. The process of claim 2 wherein $R^1$ and $R^2$ are independently selected from the group consisting of alkyl, cycloalkyl and aryl groups having up to 40 carbon atoms.

4. The process of claim 3 wherein $R^1$ and $R^2$ are independently selected from the group consisting of ethyl, butyl, pentyl, hexyl, 2-ethylhexyl, octyl, decyl, dodecyl, octadecyl, cyclopentyl, cyclohexyl, cycloheptyl, phenyl, naphthyl, and anthracenyl.

5. The process of claim 4 wherein said alkyl and cycloalkyl groups are substituted with up to two substituents selected from the group consisting of alkoxy, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, and sulfonate salts.

6. The process of claim 1 wherein said $R^1$ and/or $R^2$ independently are selected from the group having the formula:

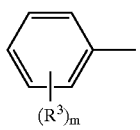

(II)

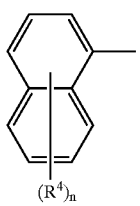

(III)

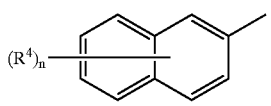

(IV)

wherein $R^3$ and $R^4$ are independently selected from the group consisting of alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid and sulfonate salts, wherein the alkyl moiety of alkyl, alkoxy, alkanoyl, alkoxycarbonyl and alkanoyloxy groups contains up to about 8 carbon atoms; m and n independently are 0, 1 or 2, wherein the total carbon atom content of the hydrocarbyl radicals represented by $R^1$ and $R^2$ is from 2 to 35 and wherein the ratio of gram moles fluorophosphite ligand to gram atoms rhodium is about 1:1 to 70:1.

7. The process of claim 1 wherein $R^1$ and $R^2$ in combination represent a divalent hydrocarbylene group containing up to about 40 carbon atoms selected from the group consisting of alkylene of about 2 to 12 carbon atoms, cyclohexylene and arylene.

8. The process of claim 7 wherein said alkylene is selected from the group consisting of ethylene, trimethylene, 1,3-butanediyl, 2,2-dimethyl-1,3-propanediyl, 1,1,2-triphenylethanediyl, 2,2,4-trimethyl-1,3-pentanediyl, and 1,2-cyclohexylene.

9. The process of claim 7 wherein said arylene groups which $R^1$ and $R^2$ collectively represent have the formula:

(V)

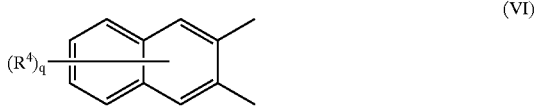

(VI)

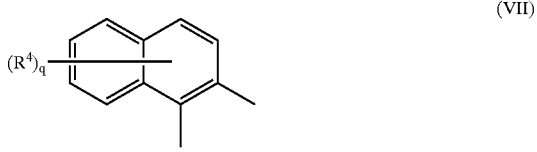

(VII)

or a radical having the formula:

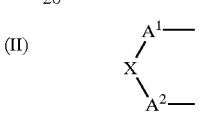

wherein $A^1$ and $A^2$ independently is an arylene radical having formula (V), (VI) or (VII) above and wherein each ester oxygen atom of fluorophosphite (I) is bonded to a ring carbon atom of $A^1$ and $A^2$;

X is: (i) a chemical bond directly between ring carbon atoms of $A^1$ and $A^2$; or (ii) an oxygen atom, a group having the formula —$(CH_2)_y$— wherein y is 2 or a group having the formula:

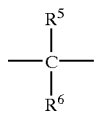

wherein $R^5$ is selected from the group consisting of hydrogen, alkyl and aryl, having formulas (II), (III) and (IV); $R^6$ is selected from the group consisting of hydrogen and alkyl, and wherein —$C(R^5)(R^6)$— has from 1 to 8 carbon atoms; and wherein $R^3$ and $R^4$ are independently selected from the group consisting of alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid and sulfonate salts wherein the alkyl moiety of such alkyl, alkoxy, alkanoyl, alkoxycarbonyl and alkanoyloxy groups contains up to about 8 carbon atoms; p and q independently are 0, 1 or 2.

10. The process of claim 1 wherein said fluorophosphite ligand has the formula:

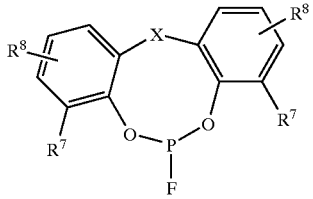

wherein $R^7$ is an alkyl having 3 to 8 carbon atoms; $R^8$ is selected from the group consisting of hydrogen, an alkyl having from 1 to 8 carbon atoms and an alkoxy having 1 to 8 carbon atoms; and X is (i) a chemical bond directly between ring carbon atoms of each phenylene group to which X is bonded; or (ii) a group having the formula:

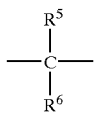

wherein $R^5$ and $R^6$ are independently selected from the group consisting of hydrogen and an alkyl having from 1 to 8 carbon atoms.

11. The process of claim 1 wherein said epoxide has the formula:

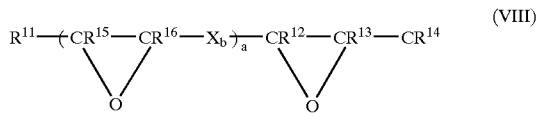

(VIII)

wherein: "a" is 0 or 1; "b" is 0 or 1; $R^{11}$–$R^{16}$ are independently selected from the group consisting of hydrogen; alkyl, aryl, aralkyl, and alkaryl groups having from 1 to about 30 carbon atoms; substituted alkyl, aryl, aralkyl and alkaryl groups having from 1 to about 30 carbon atoms; and groups wherein two or more of $R^{11}$–$R^{16}$ groups are linked together to form a cyclic structure which has up to about 30 carbon atoms; and X is a divalent bridging group selected from the group consisting of substituted or unsubstituted alkylene, arylene, aralkylene, and alkarylene groups having up to about 30 carbon atoms, —O—, —S—, —$NR^{19}$—, —$SiR^{20}$ $R^{21}$, and —CO— and wherein each radical $R^{19}$, $R^{20}$, and $R^{21}$ individually is selected from the group consisting of H and alkyl groups.

12. The process of claim 1 wherein said epoxide has the formula:

(IX)

wherein $R^{11}$–$R^{14}$ are independently selected from the group consisting of hydrogen; alkyl, aryl, aralkyl, and alkaryl groups having from 1 to about 30 carbon atoms, and substituted alkyl, aryl, aralkyl and alkaryl groups having from 1 to about 30 carbon atoms.

13. The process of claim 12 wherein at least one ring in a cyclic structure is formed by the combination of one of $R^{11}$ and $R^{12}$ groups with one of $R^{13}$ and $R^{14}$ groups.

14. The process of claim 1 wherein said epoxide is selected from the group consisting of 1,2-cyclohexene oxide; styrene oxide; propylene oxide; 1,2-epoxyoctane; 1,2-epoxydecane; 1,2-epoxydodecane; 1,2-epoxyhexadecaneoxide; 1,2-epoxyoctadecane; ethylene oxide; 1,2-cyclododecene oxide; stilbene oxide; isobutylene oxide; 2,3-epoxybutane; 1,2-epoxybutane; 1,2-epoxyhexane; 1,2-epoxydodecane; cyclopentene oxide; cyclooctene oxide; cyclodecene oxide; 1,2-epoxy-3-phenoxy-propane; β-pinene oxide; 1,3-butadiene diepoxide; 1,2,7,8-diepoxyoctane; diepoxycyclooctane; dicyclopentadiene dioxide; 3,4-epoxy cyclohexyl methyl-3,4-epoxy cyclohexyl carboxylate; vinylcyclohexene diepoxide; and hydroquinone bisglycidyl ether.

15. A process for stabilizing a fluorophosphite ligand in a hydroformylation reaction mixture having an α-olefin, hydrogen, carbon monoxide and a catalyst composition having a combination of a rhodium containing compound and one or more fluorophosphite compounds having the general formula:

(I)

wherein $R^1$ and $R^2$ are hydrocarbyl radicals which contain a total of up to about 40 carbon atoms, said process comprising adding to the reaction mixture from about 0.001 to about 1.0 weight % of an epoxide, wherein the weight % is based on the total weight of the reaction mixture.

16. The process of claim 15 wherein said rhodium containing compound is selected from the group consisting of di-rhodium tetraacetate dihydrate, rhodium(II) acetate, rhodium(II) isobutyrate, rhodium(II) 2-ethylhexanoate, rhodium(II) benzoate, rhodium(II) octanoate, $Rh_4 (CO)_{12}$, $Rh_6 (CO)_{16}$ and rhodium(I) acetylacetonate dicarbonyl.

17. The process of claim 15 wherein $R^1$ and $R^2$ are independently selected from the group consisting of ethyl, butyl, pentyl, hexyl, 2-ethylhexyl, octyl, decyl, dodecyl, octadecyl, cyclopentyl, cyclohexyl, cycloheptyl, phenyl, naphthyl, anthracenyl and aryl group having the formula:

(II)

(III)

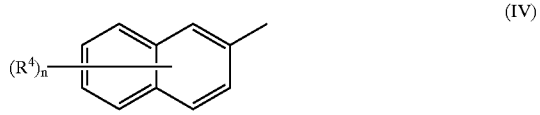

(IV)

wherein $R^3$ and $R^4$ are independently selected from the group consisting of alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid and sulfonate salts, wherein the alkyl moiety of alkyl, alkoxy, alkanoyl, alkoxycarbonyl and alkanoyloxy groups contains up to about 8 carbon atoms; m and n independently are 0, 1 or 2, wherein the total carbon atom content of the hydrocarbyl radicals represented by $R^1$ and $R^2$ is from 2 to 35 and wherein the ratio of gram moles fluorophosphite ligand to gram atoms rhodium is about 1:1 to 70:1.

18. The process of claim 15 wherein $R^1$ and $R^2$ in combination is selected from the group consisting of ethylene, trimethylene, 1,3-butanediyl, 2,2-dimethyl-1,3-propanediyl, 1,1,2-triphenylethanediyl, 2,2,4-trimethyl-1,3-pentanediyl, and 1,2-cyclohexylene, a cyclohexylene, and an arylene group having the formula:

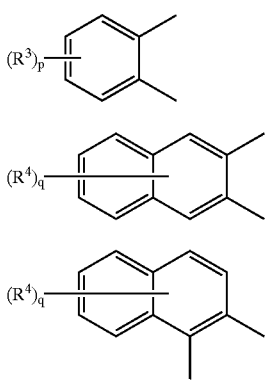

or a radical having the formula:

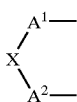

wherein $A^1$ and $A^2$ independently is an arylene radical having formula (V), (VI) or (VII) above and wherein each ester oxygen atom of fluorophosphite (I) is bonded to a ring carbon atom of $A^1$ and $A^2$;

X is (i) a chemical bond directly between ring carbon atoms of $A^1$ and $A^2$; or (ii) an oxygen atom, a group having the formula $-(CH_2)_y-$ wherein y is 2 or a group having the formula:

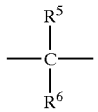

wherein $R^5$ is selected from the group consisting of hydrogen, alkyl and aryl, having formulas (II), (III) and (IV); $R^6$ is selected from the group consisting of hydrogen and alkyl, and wherein $-C(R^5)(R^6)-$ has from 1 to 8 carbon atoms; and wherein $R^3$ and $R^4$ are independently selected from the group consisting of alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid and sulfonate salts wherein the alkyl moiety of such alkyl, alkoxy, alkanoyl, alkoxycarbonyl and alkanoyloxy groups contains up to about 8 carbon atoms; p and q independently are 0, 1 or 2.

19. The process of claim 15 wherein said epoxide has the formula:

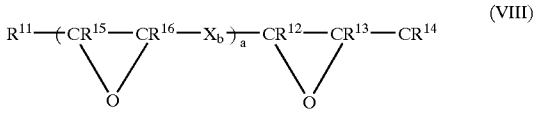

wherein: "a" is 0 or 1; "b" is 0 or 1; $R^{11}-R^{16}$ are independently selected from the group consisting of hydrogen; alkyl, aryl, aralkyl, and alkaryl groups having from 1 to about 30 carbon atoms; substituted alkyl, aryl, aralkyl and alkaryl groups having from 1 to about 30 carbon atoms; and groups wherein two or more of $R^{11}-R^{16}$ groups are linked together to form a cyclic structure which has up to about 30 carbon atoms; and X is a divalent bridging group selected from the group consisting of substituted or unsubstituted alkylene, arylene, aralkylene, and alkarylene groups having up to about 30 carbon atoms, $-O-$, $-S-$, $-NR^{19}-$, $-SiR^{20}R^{21}$, and $-CO-$ and wherein each radical $R^{19}$, $R^{20}$, and $R^{21}$ individually is selected from the group consisting of H and alkyl groups.

20. The process of claim 15 wherein said epoxide has the formula:

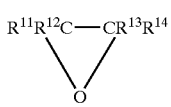

wherein $R^{11}-R^{14}$ are independently selected from the group consisting of hydrogen; alkyl, aryl, aralkyl, and alkaryl groups having from 1 to about 30 carbon atoms, and substituted alkyl, aryl, aralkyl and alkaryl groups having from 1 to about 30 carbon atoms.

21. The process of claim 20 wherein at least one ring in a cyclic structure is formed by the combination of one of $R^{11}$ and $R^{12}$ groups with one of $R^{13}$ and $R^{14}$ groups.

22. The process of claim 15 wherein said epoxide is selected from the group consisting of 1,2-cyclohexene oxide; styrene oxide; propylene oxide; 1,2-epoxyoctane; 1,2-epoxydecane; 1,2-epoxydodecane; 1,2-epoxyhexadecane oxide; 1,2-epoxyoctadecane; ethylene oxide; 1,2-cyclododecene oxide; stilbene oxide; isobutylene oxide; 2,3-epoxybutane; 1,2-epoxybutane; 1,2-epoxyhexane; 1,2-epoxydodecane; cyclopentene oxide; cyclooctene oxide; cyclodecene oxide; 1,2-epoxy-3-phenoxy-propane; β-pinene oxide; 1,3-butadiene diepoxide; 1,2,7,8-diepoxyoctane; diepoxycyclooctane; dicyclopentadiene dioxide; 3,4-epoxy cyclohexyl methyl-3,4-epoxy cyclohexyl carboxylate; vinylcyclohexene diepoxide; and hydroquinone bisglycidyl ether.

23. The process of claim 15 wherein the amount of said epoxide in said reaction mixture is from about 0.01 to about 0.8 weight %, based on the total weight of the reaction mixture.

24. A process for stabilizing a,fluorophosphite ligand in a hydroformylation reaction mixture having an α-olefin, hydrogen, carbon monoxide and a catalyst composition having a combination of a rhodium containing compound and one or more fluorophosphite compounds having the general formula:

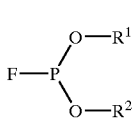

said process comprising adding to the reaction mixture from about 0.001 to about 1.0 weight % of an epoxide wherein the weight % of the epoxide is based on the total weight of the reaction mixture and wherein:

a) $R^1$ and $R^2$ are independently selected from the group consisting of ethyl, butyl, pentyl, hexyl, 2-ethylhexyl, octyl, decyl, dodecyl, octadecyl, cyclopentyl, cyclohexyl, cycloheptyl, phenyl, naphthyl, anthracenyl and aryl group having the formula:

(II)

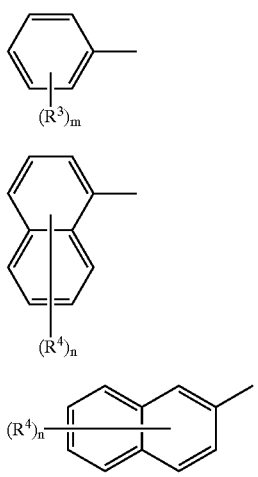

(III)

(IV)

wherein $R^3$ and $R^4$ are independently selected from the group consisting of alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid and sulfonate salts, wherein the alkyl moiety of alkyl, alkoxy, alkanoyl, alkoxycarbonyl and alkanoyloxy groups contains up to about 8 carbon atoms; m and n independently are 0, 1 or 2, wherein the total carbon atom content of the hydrocarbyl radicals represented by $R^1$ and $R^2$ is from 2 to 35 and wherein the ratio of gram moles fluorophosphite ligand to gram atoms rhodium is about 1:1 to 70:1; or b) $R^1$ and $R^2$ in combination is selected from the group consisting of ethylene, trimethylene, 1,3-butanediyl, 2,2-dimethyl-1,3-propanediyl, 1,1,2-triphenylethanediyl, 2,2,4-trimethyl-1,3-pentanediyl, and 1,2-cyclohexylene, a cyclohexylene, and an arylene group having the formula:

(V)

(VI)

(VII)

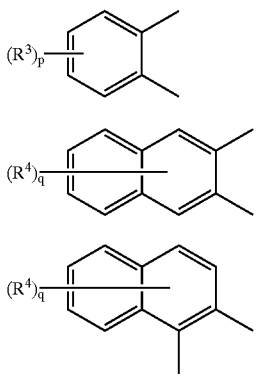

or a radical having the formula:

wherein $A^1$ and $A^2$ independently is an arylene radical having formula (V), (VI) or (VII) above and wherein each ester oxygen atom of fluorophosphite (I) is bonded to a ring carbon atom of $A^1$ and $A^2$;

X is (i) a chemical bond directly between ring carbon atoms of $A^1$ and $A^2$; or (ii) an oxygen atom, a group having the formula —(CH$_2$)$_y$— wherein y is 2 or a group having the formula:

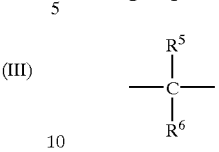

wherein $R^5$ is selected from the group consisting of hydrogen, alkyl and aryl, having formulas (II), (III) and (IV); $R^6$ is selected from the group consisting of hydrogen and alkyl, and wherein —C($R^5$)($R^6$)— has from 1 to 8 carbon atoms; and wherein $R^3$ and $R^4$ are independently selected from the group consisting of alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid and sulfonate salts wherein the alkyl moiety of such alkyl, alkoxy, alkanoyl, alkoxycarbonyl and alkanoyloxy groups contains up to about 8 carbon atoms; p and q independently are 0, 1 or 2.

25. The process of claim 24 wherein said epoxide has the formula:

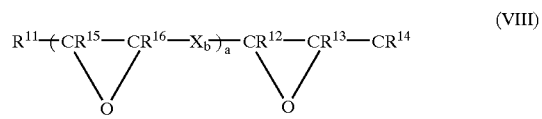

(VIII)

wherein: "a" is 0 or 1; "b" is 0 or 1; $R^{11}$–$R^{16}$ are independently selected from the group consisting of hydrogen; alkyl, aryl, aralkyl, and alkaryl groups having from 1 to about 30 carbon atoms; substituted alkyl, aryl, aralkyl and alkaryl groups having from 1 to about 30 carbon atoms; and groups wherein two or more of $R^{11}$–$R^{16}$ groups are linked together to form a cyclic structure which has up to about 30 carbon atoms; and X is a divalent bridging group selected from the group consisting of substituted or unsubstituted alkylene, arylene, aralkylene, and alkarylene groups having up to about 30 carbon atoms, —O—, —S—, —NR$^{19}$—, —SiR$^{20}$ R$^{21}$, and —CO— and wherein each radical $R^{19}$, $R^{20}$, and $R^{21}$ individually is selected from the group consisting of H and alkyl groups.

26. The process of claim 24 wherein said epoxide has the formula:

(IX)

wherein $R^{11}$–$R^{14}$ are independently selected from the group consisting of hydrogen; alkyl, aryl, aralkyl, and alkaryl groups having from 1 to about 30 carbon atoms, and substituted alkyl, aryl, aralkyl and alkaryl groups having from 1 to about 30 carbon atoms.

* * * * *